United States Patent [19]

Lewis

[11] Patent Number: 4,836,534
[45] Date of Patent: Jun. 6, 1989

[54] BACK SUPPORT APPARATUS

[76] Inventor: Trevor A. Lewis, 5 John Street, Milpara, Albany, Western Australia, Australia

[21] Appl. No.: 105,719

[22] Filed: Oct. 6, 1987

[30] Foreign Application Priority Data

Oct. 7, 1986 [AU] Australia ............... PH8376

[51] Int. Cl.$^4$ .............................. A63G 9/00
[52] U.S. Cl. .................................... 272/85
[58] Field of Search ........... 128/68, 69, 70, 71, 128/73, 75, 101.1, 25 R, 78, 132 R, 134; 272/126, 137, 143; 248/610, 76, 78; 182/3-9, 231, 232-235

[56] References Cited

U.S. PATENT DOCUMENTS

| 1,061,669 | 5/1913 | Hawk | 248/610 |
| 1,097,097 | 5/1914 | Jensen | 248/610 |
| 3,420,522 | 1/1969 | Elliott | 272/85 |
| 3,528,657 | 9/1970 | Krupsky | 272/85 |
| 4,296,836 | 10/1981 | Cooper | 182/7 |
| 4,704,749 | 11/1987 | Aubert | 5/83 |

OTHER PUBLICATIONS

Playthings, Sep. 1968, Swing Gym, p. 69.

Primary Examiner—Robert A. Hafer
Assistant Examiner—Charles H. Sam
Attorney, Agent, or Firm—Reising, Ethington, Barnard, Perry & Milton

[57] ABSTRACT

A back support comprising a frame having a first end and a second end displaced from the first end, to define a gap, a resilient member attached adjacent the first end and arranged to resiliently support the frame with the first end disposed above the second end and a belt attached in spread manner to the frame, the gap in the frame being dimensioned to allow a user to pass through it into and out of the frame.

12 Claims, 2 Drawing Sheets

BACK SUPPORT APPARATUS

The present invention relates to a back support apparatus particularly envisaged for use by persons engaged in activities requiring adopting a bent over posture.

In general, activities requiring a person to adopt a bent over posture lead to excessive strain being developed in the lower back of the person and possibly resulting in serious lower abdominal injuries. Such activities include shearing, bricklaying, gardening and the like.

It is known to provide a back support apparatus having a harness to be fitted to a torso of a user and a cord attached to the harness to resist downward movement of the user. Such harnesses are intended to be worn by the user throughout an activity requiring bending and are not intended to be entered or exited other than at the commencement and completion of the activity.

It is also known to provide a back support apparatus having a support strap or belt which is intended to rest against the users torso. Such back support apparatus comprise a frame with the support strap or belt spread between outer ends of the frame and intended to allow the user to enter and exit the back support apparatus during the activity. However, such frame/belt systems encompass the user and do not allow the user to maintain a grip on an object through the activity. For example, the hold that the user has on the object must be relinquished entirely or in part in order for the user to exit or enter the back support apparatus.

Accordingly, where the activity is shearing, a shearer may have to release one or both of his/her hands from a sheep in order to enter or exit such prior art back support apparatus. Such release of grip may allow the sheep to escape from the shearer.

Such problem is made worse by the inherent difficulty of entering or exiting the prior art type back support apparatus. That is, the time required to make such a manouevre and the intricacy involved therewith.

The present invention provides a back support apparatus which allows for side entry and exit by a user.

In accordance with the present invention there is provided a back support comprising a frame having a first end and a second end displaced from the first end to define a gap, a resilient member attached adjacent the first end and arranged to resiliently support the frame with the first end disposed above the second end and a belt attached in spread manner to the frame, the gap in the frame being dimensioned to allow a user to pass through it into and out of the frame.

The present invention will now be described by way of example with reference to the accompanying drawings in which.

Figure 1:
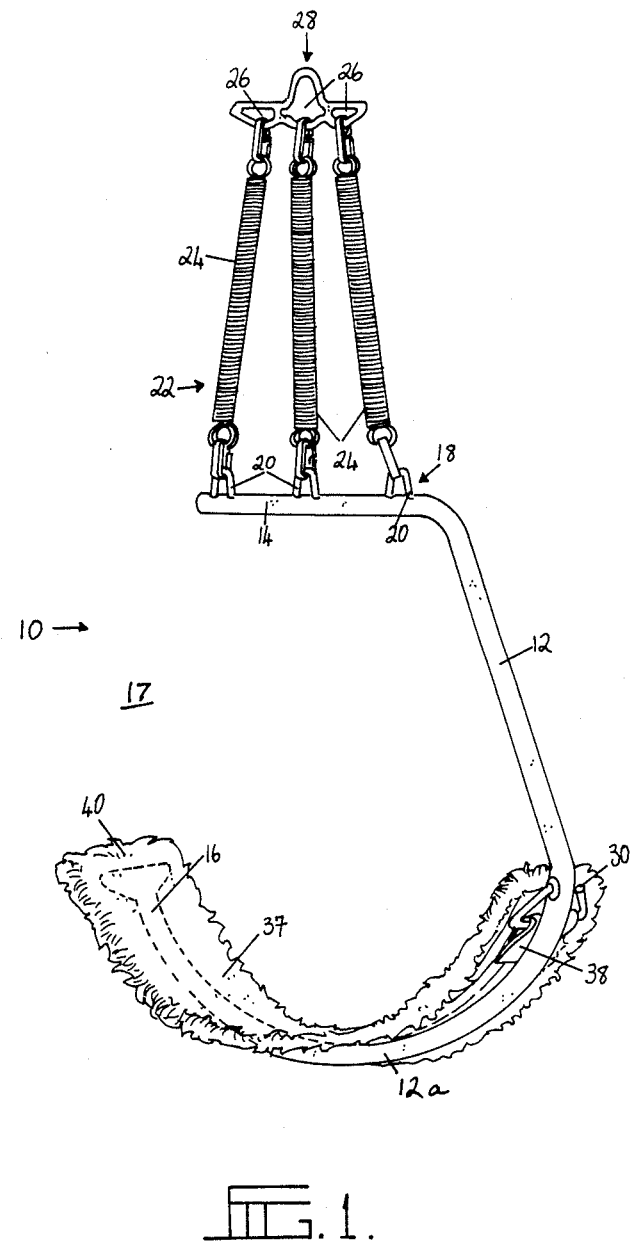
FIG. 1 is an upper rear perspective view of a back support apparatus in accordance with the present invention.

In FIG. 1 there is shown a back support apparatus 10 comprising a frame 12 having a first end 14 and a second end 16. The frame 12 is conveniently made of metal materials such as, for example, stainless steel. The frame 12 has a generally curvilinear shape between the first end 14 and the second end 16. The first end 14 and the second end 16 are spaced apart and define a gap 17 located at a side of the back support apparatus 10. The gap 17 is dimensioned to allow passage of a torso of a user through it into and out of the frame 12.

The first end 14 is disposed oppositely of the second end 16 and each directed in the same general direction and preferably directed in intersecting aspect such that lines drawn in the direction of the first and second ends 14 and 16 intercept, as can be seen in FIG. 1.

The frame 12 also comprises the cradle portion 12a located adjacent the second end 16 and intermediately between the first end 14 and the second end 16. The cradle portion 12a preferably extends away from the gap 17 and is generally concave when viewed from the gap 17, as can be seen in FIG,. 1. The cradle portion 12a is directly beneath the first end 14 of the frame 12.

The frame 12 comprises a fixing means 18 at or adjacent the first end 14. The fixing means 18 is conveniently formed from three spaced apart loops 20.

The fixing means 18 is constructed to provide securement for a resilient member 22, here conveniently comprising three springs 24. The springs 24 are in turn each attached to a corresponding eye 26 of a gamble 28 arranged to be fixed to an object such as a beam or the like to restrain the back support apparatus 10, when in use.

The spring 24 disposes the first end 14 directly and vertically above and over the second end 16 and the second end 16 underlies or is beneath the first end 14 as shown in FIG. 1.

Figure 2:
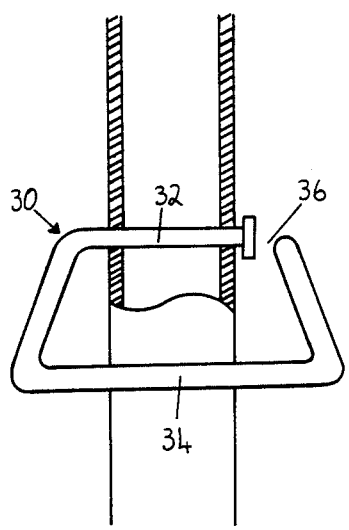
FIG. 2 is a part section view of a buckle of the back support apparatus of FIG. 1 shown fixed to a frame thereof.

Preferably, adjacent ones of the loops 20 are mutually further apart than adjacent ones of the eyes 26. Such arrangement has been found preferable to reduce the likelihood of adjacent ones of the springs 24 becoming entangled and thus obviating the need for a shield over one or all of the springs 24. The back support apparatus 10 also comprises a buckle 30 particularly as shown in FIG. 2. The buckle 30 is conveniently in the form of a "G" shaped rod comprising an axle portion 32 fixed in a hole in the frame 12 intermediate of the first end 14 and the second end 16.

The buckle 30 also comprises a toe portion 34 extending from the axle 32 at one end, adjacent to the axle 32 at an other end.

A gap 36 is formed between the axle 32 and the other end of the toe 34.

The back support 10 comprises a belt 37 having a first looped end 38 and a second pocket end 40. The looped end 38 is constructed to be fixed to the buckle 30 and the pocket end 40 is constructed to be fixed to the second end 16 of the frame 12 as shown in FIG. 1.

That is the looped end 38 and the pocket end 40 are attached to the cradle portion 12a as shown in FIG. 1, and that the belt 37 overlies the cradle portion 12a.

Figure 3:
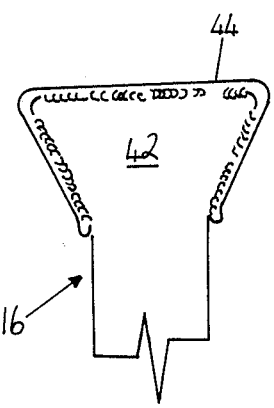
FIG. 3 is a front elevation of a second end of the frame of the back support apparatus of FIG. 1.

As shown in FIG. 3, the second end 16 of the frame 12 is preferably flattened to form a web 42 and provided with a rounded lip 44. The second end 16 is thus of a shape preferred to be received in the pocket end 40 of the belt 37. It is envisaged that the belt 37 could be attached to the frame 12 other than at the second end 16, such as, for example, adjacent the second end 16.

In use, the back support apparatus 10 has its gamble 28 fixed to an object such as a beam of a building, or a bracket constructed for the purpose or the like. The springs 24 and the frame 12 are thus suspended below the gamble 28 and to a height above a floor of the building, or the ground below the beam. The height of the gamble 28 is then adjusted, such as by use of chain links, so that the belt 37 approximately corresponds with the torso of a user.

The user enters the back support apparatus 10 through the gap 17 between the first end 14 and the second end 16 by first pushing the belt 37 and/or the frame 12 down with his or her hand. The user then positions the belt 37 against a convenient region of his or her torso.

When the user bends over, the belt 37 and hence the frame 12 are forced downwardly and the force results in extension of the springs 24, which extension opposes the downward force. Accordingly, the back support apparatus 10 supports, at least in part, the user whilst he or she is in a bent over position. The user may exit the back support apparatus 10 by pushing the belt 37 and/or the frame 12 down with his or her hand and exiting through the gap 17 between the first and second ends 14 and 16.

The back support apparatus 10 may also be used to assist in lifting and dragging objects, such as, for example, by a shearer retrieving sheep to be shorn from a nearby holding pen.

Use of the back support apparatus 10 of the present invention results in substantially reduced strain on the back of the user and also affords ready, simple and convenient entry and exit via the gap between the first and second ends 14 and 16. Since the frame 12 and the belt 37 do not encompass the user more rapid entry and exit of the back support apparatus 10 of the present invention is possible.

Such ease and speed of entry and exit allows the user greater control over a sheep which is to be or is in the process of being shorn for example. Prior art back support apparatus all rely on closed harnesses and the like and are difficult and relatively slow to exit from and enter into thus reducing the control that the user has on a sheep.

The splaying of the springs 24 alleviates tangling which plagues prior art support apparatus. Such tangling tends to occur in parallel disposed springs when the springs are extended and the user twists a frame of the apparatus with respect to a gamble or the like.

Modifications and variations such as would be apparent to a skilled addressee are deemed within the scope of the present invention. For example, a number of springs 24 other than three could be used. Also, the springs 24 could be replaced by shock cord.

The claims defining the invention are as follows:

1. A back support comprising; a frame of generally curvilinear shape having a first end and a second end, a gap formed between said first and said second ends of said frame and dimensioned to allow a user to pass into and out of said frame through said gap, a resilient member attached adjacent said first end and arranged to resiliently support said frame with said first end disposed above said second end, a belt having a first end attached to said frame intermediately between said first end of said frame and said second end of said frame and said belt having a second end attached to said frame adjacent said second end of said frame such that said first end of said belt and said second end of said belt are fixed at substantially equal heights along said frame and said belt is disposed directly underneath said first end of said frame.

2. A back support apparatus according to claim 1, in which said belt includes a pocket end constructed to fit over said second end of said frame.

3. A back support apparatus according to claim 1, including a gamble, said resilient member comprising one or more springs fixed to said frame at a first end and fixed to said gamble at a second end remote from said first end of said resilient member.

4. A back support apparatus according to claim 3, in which said resilient member comprises a plurality of said springs, having adjacent springs in splayed relation between said frame and said gamble.

5. A back support apparatus according to claim 1, in which said frame comprises a buckle having an axle positioned through said frame intermediately of said second end of said frame, a toe portion extending from said axle and a gap formed between said toe and said frame, said gap of said buckle being dimensioned to receive said first end of said belt.

6. A back support apparatus according to claim 5, in which said first end of said belt comprises a loop to be attached to said buckle via said gap of said buckle.

7. A back support comprising:
   (i) a frame of generally curvilinear shape having:
      (a) a first end;
      (b) a second end, said second end being disposed oppositely of said first end and each of said first and said second ends directed in the same general direction;
      (c) a gap formed between said first and said second ends and dimensioned to allow a user to pass into and out of said frame through said gap; and
      (d) a cradle portion located adjacent said second end and intermediately between said first end and said second end, said cradle portion being generally concave when viewed from said gap;
   (ii) a resilient member attached to said frame adjacent said first end and arranged to resiliently dispose said frame with said first end disposed vertically above said cradle portion and said cradle portion directly beneath said first end, and
   (iii) a belt having:
      (a) a first end attached to said cradle portion intermediately between said first and said second ends of said frame; and
      (b) a second end attached to said cradle portion adjacent said second end of said frame; such that said first and said second ends of said belt are fixed at substantially equal heights on said frame and said belt overlying said cradle portion to bear against a torso of the user in a non-encompassing manner.

8. A back support apparatus according to claim 7, in which said belt includes a pocket end constructed to fit over said second end of said frame.

9. A back support apparatus according to claim 7, including a gamble, said resilient member comprises one or more springs fixed to said frame at a first end and fixed to said gamble at a second end remote from said first end of said resilient member.

10. A back support apparatus according to claim 9, in which said resilient member comprises a plurality of said springs having adjacent springs in splayed relation between said frame and said gamble to avoid entanglement of said springs when same are extended.

11. A back support apparatus according to claim 7, in which said frame comprises a buckle having an axle positioned through said frame intermediately of said second end of said frame, a toe portion extending from said axle and a gap formed between said toe and said frame, said gap of said buckle being dimensioned to receive said first end of said belt.

12. A back support apparatus according to claim 11 in which said first end of said belt comprises a loop to be attached to said buckle via said gap of said buckle.

* * * * *